United States Patent
Howell

(10) Patent No.: US 11,117,128 B2
(45) Date of Patent: Sep. 14, 2021

(54) FILTRATION DEVICE

(71) Applicant: Vanadis Diagnostics, Sollentuna (SE)

(72) Inventor: Mathias Howell, Uppsala (SE)

(73) Assignee: VANADIS DIAGNOSTICS AB, Sollentuna (SE)

( * ) Notice: Subject to any disclaimer, the term of this patent is extended or adjusted under 35 U.S.C. 154(b) by 345 days.

(21) Appl. No.: 16/109,633

(22) Filed: Aug. 22, 2018

(65) Prior Publication Data

US 2019/0060894 A1 Feb. 28, 2019

Related U.S. Application Data

(60) Provisional application No. 62/550,478, filed on Aug. 25, 2017.

(51) Int. Cl.
*B01D 61/18* (2006.01)
*B01D 69/06* (2006.01)
(Continued)

(52) U.S. Cl.
CPC .......... *B01L 3/50255* (2013.01); *B01D 61/18* (2013.01); *B01D 63/081* (2013.01); *B01D 63/088* (2013.01); *B01D 65/003* (2013.01); *B01D 71/025* (2013.01); *B01J 19/0046* (2013.01); *C12M 23/12* (2013.01); *B01D 69/06* (2013.01); *B01D 71/04* (2013.01); *B01D 2313/04* (2013.01); *B01D 2313/143* (2013.01); *B01J 2219/00639* (2013.01);
(Continued)

(58) Field of Classification Search
None
See application file for complete search history.

(56) References Cited

U.S. PATENT DOCUMENTS 5,854,033 A 12/1998 Lizardi
6,037,168 A * 3/2000 Brown ................ B01L 3/50853
435/288.3
(Continued)

FOREIGN PATENT DOCUMENTS

CN 102827929 6/2014
EP 1284816 B1 8/2009
(Continued)

OTHER PUBLICATIONS

Durtschi et al., "Increased sensitivity of bacterial detection in cerebrospinal fluid by fluorescent staining on low-fluorescence membrane filters" Journal of Medical Microbiology, 2005, pp. 843-850, vol. 54.

(Continued)

*Primary Examiner* — Matthew D Krcha
*Assistant Examiner* — Brittany I Fisher
(74) *Attorney, Agent, or Firm* — James S. Keddie; Bozicevic, Field & Francis LLP

(57) ABSTRACT

This disclosure provides, among other things, a filtration device comprising an open bottomed multi-well plate, a planar spacer that comprises apertures, and a porous capillary membrane. In the device, the planar spacer is sandwiched between the multi-well plate and the porous capillary membrane and the planar spacer is bonded to both the multi-well plate and the porous capillary membrane via an adhesive. Kits and methods of making the device are also provide.

20 Claims, 3 Drawing Sheets

(51) Int. Cl.

| | |
|---|---|
| *B01L 3/00* | (2006.01) |
| *B01D 65/00* | (2006.01) |
| *B01D 63/08* | (2006.01) |
| *C12M 1/32* | (2006.01) |
| *B01D 71/02* | (2006.01) |
| *B01J 19/00* | (2006.01) |
| B01D 71/04 | (2006.01) |
| G01N 1/40 | (2006.01) |

(52) U.S. Cl.
CPC ... *B01L 2200/0689* (2013.01); *B01L 2200/12* (2013.01); *B01L 2200/141* (2013.01); *B01L 2300/0681* (2013.01); *B01L 2300/0829* (2013.01); *B01L 2300/0851* (2013.01); *B01L 2300/0887* (2013.01); *G01N 1/40* (2013.01); *G01N 2001/4088* (2013.01)

(56) References Cited

U.S. PATENT DOCUMENTS

| | | | | |
|---|---|---|---|---|
| 6,376,256 | B1* | 4/2002 | Dunnington | B01J 19/0046 209/45 |
| 6,483,640 | B1* | 11/2002 | Tonucci | B82Y 20/00 343/895 |
| 7,736,594 | B1 | 6/2010 | Grudzien et al. | |
| 2003/0026739 | A1 | 2/2003 | MacBeath et al. | |
| 2003/0096268 | A1 | 5/2003 | Weiner et al. | |
| 2003/0198576 | A1* | 10/2003 | Coyne | B01F 5/0646 422/400 |
| 2004/0141887 | A1 | 7/2004 | Mainquist et al. | |
| 2005/0009022 | A1 | 1/2005 | Weiner et al. | |
| 2005/0052646 | A1* | 3/2005 | Wohlstadter | B01L 9/50 356/311 |
| 2006/0134397 | A1 | 6/2006 | Smith | |
| 2006/0228813 | A1 | 10/2006 | Wu et al. | |
| 2007/0034140 | A1* | 2/2007 | Thorne | C30B 29/58 117/68 |
| 2008/0287307 | A1 | 11/2008 | Adrien et al. | |
| 2010/0047773 | A1 | 2/2010 | Erland et al. | |
| 2010/0093557 | A1 | 4/2010 | Kumble | |
| 2012/0328488 | A1* | 12/2012 | Puntambekar | B01L 3/50273 422/503 |
| 2013/0323729 | A1 | 12/2013 | Zhejiang | |
| 2014/0204464 | A1* | 7/2014 | Halverson | G02F 1/133524 359/599 |

FOREIGN PATENT DOCUMENTS

| | | |
|---|---|---|
| EP | 2420824 A2 | 2/2012 |
| WO | WO 2010/044083 A2 | 4/2010 |
| WO | 20110142836 | 11/2011 |
| WO | 20120019200 | 2/2012 |
| WO | 2015083001 | 6/2012 |
| WO | 2015083002 | 6/2015 |
| WO | WO 2016/174649 | 11/2016 |
| WO | WO 2017/046775 | 3/2017 |

OTHER PUBLICATIONS

Ingham et al., "Where bio meets nano: The many uses for nanoporous aluminum oxide in biotechnology" Biotechnology Advances, 2012, pp. 1089-1099, vol. 30.

Poinern et al., "Progress in Nano-Engineered Anodic Aluminum Oxide Membrane Development" Materials, 2011, pp. 487-526, vol. 4.

Santos et al., "Nanoporous anodic aluminum oxide for chemical sensing and biosensors" Trends in Analytical Chemistry, Mar. 2013, p. 25-38, vol. 44.

Tanaka et al., "Single-Molecule DNA Patterning and Detection by Padlock Probing and Rolling Circle Amplification in Microchannels for Analysis of Small Sample Volumes" Analytical Chemistry, 2011, pp. 3352-3357, vol. 83.

Van Beuningen et al., "Fast and specific hybridization using flow-through microarrays on porous metal oxide" Clinical Chemistry, 2001, pp. 1931-1933, vol. 47.

Whatman Anodisc inorganic filter membrane, WHA68095012, 2018, p. 1-3.

Koltai et al., "Survey and Summary Specificity of DNA microarray hybridization: characterization, effectors and approaches for data correction", Nucleic Acids Research, 2008, 36(7): 2395-2405.

Chen et al., "Charge dynamic characteristics in corona-charged polytetrafluoroethylene film electrets", Journal of Zhejiang University Science, 2004, abstract only.

Composite Envisions, product literature for "Non Porous Teflon Coated Release Film with Silicone Adhesive 39.37"/1000mm with Thickness .007"/.18mm", downloaded from https://compositeenvisions.com/non-porous-teflon-coated-release-film-with-silicone-adhesive-39-37-100cm-width-thickness-007-18mm/ on May 14, 2021.

Lamb et al., "A composition of porous and non-porous teflon membranes plus demineralized freeze-dried bone allograft in the treatment of class II buccal/lingual furcation defects: a clinical reentry study", J. Periodontol., 2001, abstract only.

Walters et al., "Comparison of Porous and Non-Porous Teflon Membranes Plus a Xenograft in the Treatment of Vertical Osseous Defects: A Clinical Reentry Study", J. Periodontol., 2003, 74(8): 1161-1168.

* cited by examiner

FILTRATION DEVICE

CROSS-REFERENCING

This application claims the benefit of provisional application Ser. No. 62/550,478, filed on Aug. 25, 2017, which application is incorporated by reference herein in its entirety.

BACKGROUND

Certain analytical methods require filtering particles through a membrane and analyzing the particles that are captured by the membrane. These methods are typically implemented by affixing a membrane onto the bottom of a container, placing the sample into the container, drawing the sample through the filter, and imaging the particles while they are retained on the filter. In theory, these methods can be implemented in a multi-well plate format. However, in practice, it can be challenging to implement such methods on a multi-well plate format because multi-well plates are typically made by molding and, as such, often contain dimples and bumps caused by the molding process and/or may be warped. These imperfections can cause the seal between the filter and the multi-well plate to be less than water-tight which, in turn, can cause the samples to bleed into one another as they pass through the filter. In addition, the imperfections can cause the filter to be not planar, which, in turn, causes the filter to go out of the focal plane of the imaging device. Both of these things can cause reduction in quality of experimental results.

SUMMARY

This disclosure provides, among other things, a filtration device comprising an open bottomed multi-well plate, a planar spacer that comprises apertures, and a porous capillary membrane. In the device, the planar spacer is sandwiched between the multi-well plate and the porous capillary membrane, and the planar spacer is bonded to both the multi-well plate and the porous capillary membrane via an adhesive. Placing a planar spacer between the multi-well plate and the membrane can, in some cases, effectively iron out the imperfections on the side of the plate that is attached to the membrane and provide a flat surface for the membrane to adhere to. Use of the present device is believed to reduce sample-to-sample contamination and increase the amount of membrane that is within the focal plane of the imaging device, thereby providing a significant advantage over devices that do not contain the spacer. Kits and methods of making the device are also provided.

BRIEF DESCRIPTION OF THE FIGURES

Some aspects of the technology described herein may be best understood from the following detailed description when read in conjunction with the accompanying drawings. It is emphasized that, according to common practice, the various features of the drawings are not to scale. Indeed, the dimensions of the various features are arbitrarily expanded or reduced for clarity. Included in the drawings are the following figures.

FIG. 1A shows an example of an open-bottomed multi-well plate, an example of a planar spacer that comprises apertures, and a porous capillary membrane. FIG. 1B is a cross-section of an example of the present device.

DETAILED DESCRIPTION

Figure 1A:
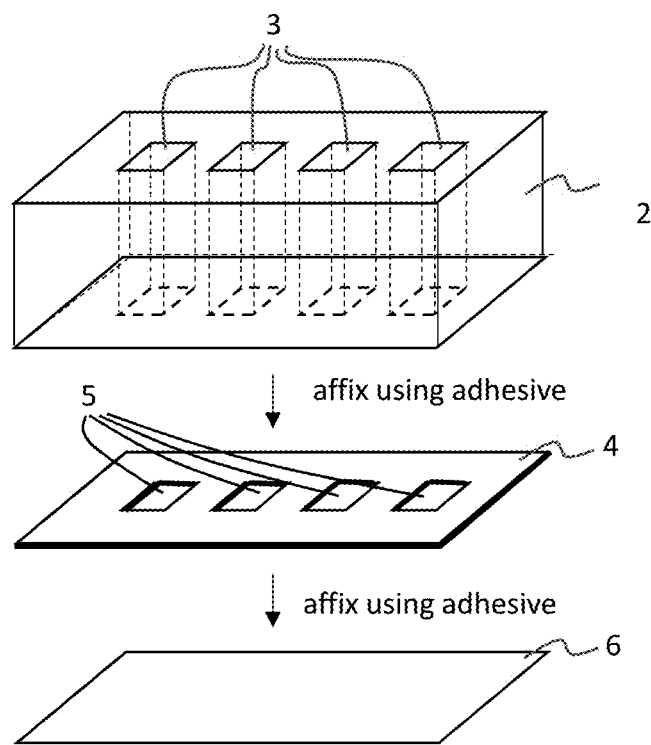
FIGS. 1A and 1B schematically illustrate examples of components that can be used to construct an embodiment of the present device.

Before embodiments of the present invention are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a nucleic acid" includes a plurality of such nucleic acids and reference to "the compound" includes reference to one or more compounds and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

All patents and publications, including all sequences disclosed within such patents and publications, referred to herein are expressly incorporated by reference.

The headings provided herein are not limitations of the various aspects or embodiments of the invention. Accordingly, the terms defined immediately below are more fully defined by reference to the specification as a whole.

Figure 1B:
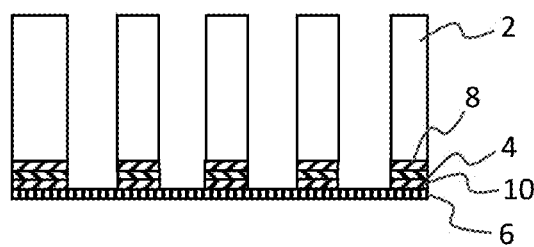
Figure 2:
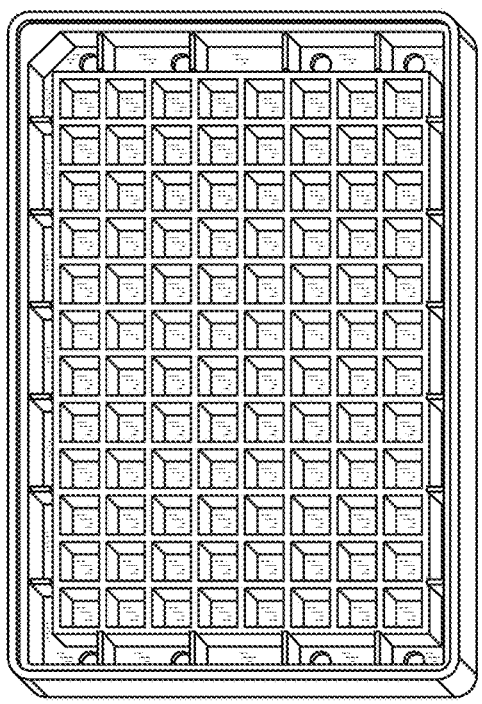
FIG. 2 shows some of the components that can be used in the present method.
Figure 2:
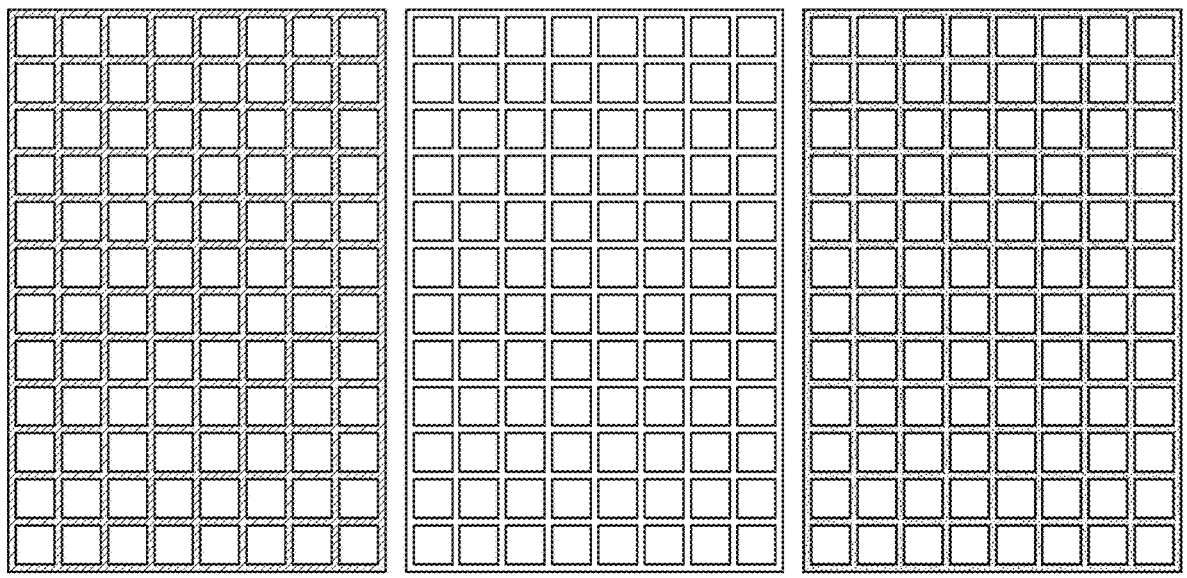

Examples of parts that can be employed in the present filtration device are shown in FIG. 1. With reference to FIG. 1, the filtration device may comprise open-bottomed multi-well plate 2, planar spacer 4 that comprises apertures 5, and porous capillary membrane 6. As shown, the positioning and size of the apertures 5 may match the positioning and size of the wells 3 of the multi-well plate. In some embodiments, the planar spacer and the capillary membrane are shaped to match the bottom of the multi-well plate. FIG. 2 shows a cross-section of the device. As shown in FIG. 2, the planar spacer is sandwiched between the multi-well plate and the porous capillary membrane, the apertures of the spacer are aligned with the wells of the multi-well plate, planar spacer 4 is bonded to multi-well plate via adhesive 8, and planar spacer 4 is bonded to porous capillary membrane 6 via adhesive 10.

The open-bottomed multi-well plate may be any particular format and, in some embodiments, may have at least 10 wells, e.g., at least 50 wells or at least 100 wells. As shown in FIG. 1A, these plates contain multiple openings ("wells") that extend from one side of the plate to the other. In some embodiments, the plate may be a 24-well, 48-well, 96-well or 384-well plate. Such plates generally have a planar bottom (except for the wells) and may be referred to as "no-bottom" or "bottomless" plates by some manufacturers. Such plates can be purchased from a variety of manufacturers, including 4titude (UK), Greiner (Kremsmünster, Austria) and E and K Scientific (Santa Clara, Calif.) and, in some cases, can be custom designed.

Multi-well plates that have irregular spacing between the wells and/or different numbers of wells (e.g., 25, 36, 49, 64, 81 or 100 wells) can be used in some cases. In many cases, the multi-well plate may be made from a polymer (i.e., may be made of a plastic) and may be molded, i.e., made by a process that involves a mold, although the plate may be made by another manufacturing process in some cases. The wells of the plate and the plate itself may be any suitable shape, including, but not limited to, round, rectangular, square and hexagonal, etc.

In some embodiments, the planar spacer may have a constant thickness in the range of 100 microns to 2 mm, e.g., in the range of 200 microns to 1.5 mm. The planar spacer may have a constant thickness and may be made by passing the material through rollers. In some embodiments, the planar spacer may be made from a metal, e.g., an alloy, nickel titanium, stainless steel or aluminum, although other materials, e.g., an extruded plastic can be used.

The porous capillary membrane is a membrane that has relatively densely packed individual capillaries that span the thickness of the membrane, i.e., that go from one side of the membrane to the other, thereby allowing the passage of liquid, but not particles, from one side of the membrane to the other. Examples of porous capillary membranes include, but are not limited to, e.g., anodic aluminum oxide membranes (see below), nanochannel glass membranes, track etched membranes and polytetrafluoroethylene. Nanochannel glass membranes are made of glass and have a high density of uniform channels with diameters from 15 microns to 15 nanometers (see, e.g., Tonucci et al., Advances in Nanophotonics II, AIP Conference Proceedings, 2007 959: 59-71; Pearson et al., Science 1995 270:68-70 and Tonucci et al., Science 1992 258: 783-785, as well as U.S. Pat. Nos. 5,306,661; 5,332,681; 5,976,444; 6,087,274; 6,376,096; 6,483,640; and 6,599,616, which are incorporated by reference). Track etched membranes are made of a transparent polymer (e.g., polycarbonate, polyethylene terephthalate or polyimide and the like) containing pores having a diameter in the range of 0.01 µm to 30 µm that have been made by a combination of charged particle bombardment (or irradiation) and chemical etching. Other porous membranes of interest include, but are not limited to, amorphous fluoropolymers such as NAFION™, TEFLON AF™, FEFLON FEIP™, and CYTOP™ (DuPont Fluoroproducts, Fayetteville, N.C.). As would be recognized, a porous capillary membrane may have a surface (e.g., a coating or a chemically modified surface) that is different to the material from which the membrane is made. For example, the surface of a porous capillary membrane may have altered charge characteristics or altered hydrophobicity or hydrophilic characteristics. In some embodiments, the surface may be coated with amino silane, poly-lysine for another compound to provide a positive charge that helps retain the fluorescent products, e.g., RCA products, to the surface. Alternatively or in addition, the surface may have a thin layer of a metal (e.g., titanium, gold) deposited therein, which can be linked to other agents that modify the surface properties of the filter. An anodic aluminum oxide membrane is a regular, self-organized nanoporous membranous structure that is produced when Al is anodized in certain acidic media. The interior diameter of the pores in the membrane, the distance between the centers of adjacent pores in the membrane, and the distance between the edges of adjacent pores in the membrane can be controlled by the voltage of the deposition, the type of acid, and other parameters. An anodic aluminum oxide membrane is virtually transparent when wet. Anodic aluminum oxide membrane, its properties, and how to make such membranes are reviewed in detail in a variety of publications including, but not limited to: Li et al. (Chem. Mater 1998 10: 2470-2480), Santos et al. (Trends on Analytical Chemistry 2013 44: 25-38), Ingham et al. (Biotechnology Advances 30 2012 1089-1099) and Poinern et al. (Materials 2011 4: 487-526), which are incorporated by reference herein for those teachings. Anodic aluminum oxide membranes are commercially available under the trade name ANOPORE™ from, e.g., SPI Supplies (West Chester, Pa.) and from other vendors such as Sykera Technologies Inc. (Longmont, Colo.), General Electric (Boston, Mass.), and Sigma-Aldrich (St. Louis, Mo.) and can be purchased with a support ring.

In some embodiments, the adhesive between the planar spacer and the multi-welled plate, i.e., adhesive 8 may be continuous around the bottom of each well to provide a liquid-tight seal that prevents well-to-well leakage between adjacent wells of the plate. In other words, adhesive 8 may provide a liquid-tight seal between the wells of the multi-well plate and the apertures of the planar spacer, thereby preventing inter-well leakage and forming a planar surface that permits the filter surfaces within the wells to substantially remain in the same focal plan of the imaging device. In some embodiments, the multi-well plate and the planar spacer are separated from each other by the adhesive, e.g., by an average distance of at least 20 microns, e.g., in the range of 50 to 300 microns.

In some embodiments, the adhesive around the planar spacer and the porous capillary membrane, i.e., adhesive 10, may be continuous around the bottom of each aperture of the planar spacer and provide a liquid-tight seal that prevents leakage between adjacent apertures of the planar spacer. In some embodiments, the planar spacer and porous capillary membrane are separated from each other by the adhesive, e.g., by an average distance of at least 10 microns, e.g., in the range of 10 microns to 100 microns.

The multi-well filtration device may be made by any suitable method. In some embodiments, the device may be made by (a) obtaining: an open bottomed multi-well plate, a porous capillary membrane, and a planar spacer that comprises apertures, as described above; (b) affixing a first side of the planar spacer to the bottom of the open bottomed multi-well plate using an adhesive; and (c) affixing the porous capillary spacer to the second side of the planar spacer using an adhesive. Steps (b) and (c) can be done in any order or at the same time.

In some embodiments, the method may be done by (a) producing a layered assembly comprising, in order, the open bottomed multi-well plate, a layer of adhesive, and a planar spacer that comprises apertures; (b) applying a force to press the multi-well plate and planar spacer together so that the multi-well plate and top of the planar spacer bond together via the adhesive; (c) removing the force; and then (d) affixing the bottom of the planar spacer to a porous capillary membrane using an adhesive.

In other embodiments, the method may be done by (a) producing a layered assembly comprising, in order, the planar spacer, a layer of adhesive, and the capillary membrane; (b) applying a force to press the planar spacer and capillary membrane together so that the planar spacer and capillary membrane bond together via the adhesive; (c) removing the force; and then (d) affixing the top of the planar spacer to the bottom of the multi-well plate using an adhesive.

In some embodiments, the method may comprise (a) producing a layered assembly comprising, in order: the open bottomed multi-well plate, adhesive, the planar spacer, adhesive, and the porous capillary membrane; (b) applying a force to press the multi-well plate and porous capillary membrane together so that the multi-well plate, planar spacer, and porous capillary membrane bond together via the adhesive; and (c) removing the force of (b), to produce the multi-well filtration device.

In any embodiment, the force may be applied to the layered assembly using a stamper that applies a force of at least 1 bar, e.g., at least 5 bar, up to about 10 bar (e.g., up to about 8 bar), to the top and/or bottom of the layered assembly, thereby forcing the components together and forming a liquid-tight seal around both sides of the apertures.

As would be apparent, any implementation of the method may comprise allowing the adhesive to set.

In some embodiments, the adhesive of (ii) may be continuous around the bottom of each well of the plate and, in some cases, may have an average thickness in the range of, e.g., 100 to 300 microns in the areas that make contact with the planar spacer.

Likewise, in some embodiments, the adhesive of (iv) may be continuous around the apertures of the spacer and, in some cases, may have an average thickness in the range of, e.g., 30 to 80 microns in the areas that make contact with the capillary membrane.

In any embodiment, the adhesive used may be implemented in a peel-and-stick format. As such, in some embodiments, the method may comprise peeling off a strip of material, e.g., a paper or plastic, from the adhesive prior to making contact with another component. In some embodiments, the peel-and-stick adhesive may be in the form of a tape (which may have, for example, a backing (e.g. a PET backing) and, on both sides of the backing, a tackified adhesive (e.g., an acrylic adhesive) covered by a protective film that can be peeled off) that has been cut to match the grid (as illustrated in FIG. 2).

Any suitable adhesive, e.g., a pressure sensitive adhesive, may be used. Suitable adhesives include, but are not limited to liquid adhesives, silicones & epoxies, UV cured adhesives and room-temperature-vulcanization (RTV) silicone adhesives. A suitable adhesive should produce a liquid tight seal when it is cured and, as should be apparent, a suitable adhesive should not dissolve in water.

The present filtration device may be used in a variety of different ways. In one example, a plurality of liquid samples that contain particles, e.g., fluorescently labeled rolling circle amplification (RCA) products, may be added to the wells and filtered through the membrane. The filtering step concentrates the particles in or on the membrane. After any optional washing/fixation steps the particles may be detected while they are on the membrane. In some embodiments, this step may produce an image of the particles. As would be apparent, the detecting may be done using any suitable fluorescence detector, e.g., a fluorescence microscope, a scanner, using a high-resolution CMOS or CCD detector or using a PMT or the like. Finally, the amount of particles in the area of the membrane is determined, e.g., by counting individually resolved particles, or by measuring an aggregate signal, etc. This determination provides an estimate of the number of the particles in the sample. As would be apparent, in any embodiment, the pores of the capillary membrane should be of sufficient size so as to prevent the particles from passing through the pores. For example, in embodiments, the pore diameter of the capillary membrane may be no more than 50% of the median diameter of the particles, while in some embodiments it may be no more than 20% of the median diameter of the particles, and in some embodiments no more than 10% of the median diameter of the particles. As such, in filtering the sample using the porous capillary membrane, the particles should remain on top of the membrane and should not fully enter or pass through the pores.

Also provided are kits. In some embodiments, a kit may comprise (a) an open bottomed multi-well plate, as described above, (b) a porous capillary membrane; as described above, and (c) a planar spacer that comprises apertures, as described above. The kit may also comprise an adhesive. In some embodiments, the planar spacer comprises a pre-applied layer of adhesive, e.g., a pressure sensitive adhesive, on one or both sides of the spacer. In these embodiments, the pre-applied layer of adhesive may be continuous around each aperture of the planar spacer on one or both sides of the planar spacer. The adhesive may be a peel-and-stick adhesive and a layer of material may be peeled from the spacer to expose the adhesive before use. In some embodiments, the kit may further comprise a double-sided peel and stick adhesive tape, cut to match the grid as illustrated in FIG. 2. In some embodiments, the planar space or tape may comprise a pre-applied layer of adhesive that has an average thickness of at least 100 microns (e.g., in the range of 150 to 300 microns) on one side and a layer of adhesive that has an average thickness in the range of less than 100 microns (e.g., in the range of 30-80 microns) on the other side. As noted above, the planar spacer and porous capillary membrane (and the adhesive, if it is a peel and stick adhesive) may be shaped to match the open bottom of the multi-well plate. In addition to above-mentioned components, the subject kits may further include instructions for using the components of the kit to practice the subject method.

Examples

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

In this experiment, the filter plates were assembled in two different ways, the "old" way (which involves affixing an aluminum oxide filter directly to an open-bottomed multi-well plate using an adhesive), and the "new" way (which involves affixing an aluminum oxide filter indirectly to an open-bottomed 96 well plate via a flat grid). In manufacturing a filter plate the old way, an approximately 200 micron layer of adhesive (3M 9088) is applied to the bottom of the plate and an aluminum oxide filter cut to match the grid is placed over the adhesive. The aluminum oxide filter and plate are then forced together by applying pressure (approximately 6 bar) using a pneumatic press. After the adhesive is set, the filter may be used. In manufacturing a filter plate the new way, a sandwich is produced that contains, in order, an open-bottomed multi-plate, an approximately 200 micron layer of adhesive, a flat stainless steel grid that is approximately 300 microns thick, a 30-80 micron layer of adhesive (Tesa 4980 or Nitto 5608BN), and an aluminum oxide filter. The aluminum oxide filter, grid and plate are then forced together by applying pressure (approximately 6 bar) using a pneumatic press. After the adhesive is set, the filter may be used. FIG. 2 shows some of the components used in the new method, where component 1 is the plate, component 2 is a peel and stick adhesive (in this case, a double-sided peel and stick tape cut into a pattern that matches the grid) that is approximately 200 microns thick, component 3 is a grid, component 5 is peel and stick adhesive (a double-sided peel and stick tape) that is approximately 80 microns thick and component 5 is an aluminum oxide filter.

Figure 3:
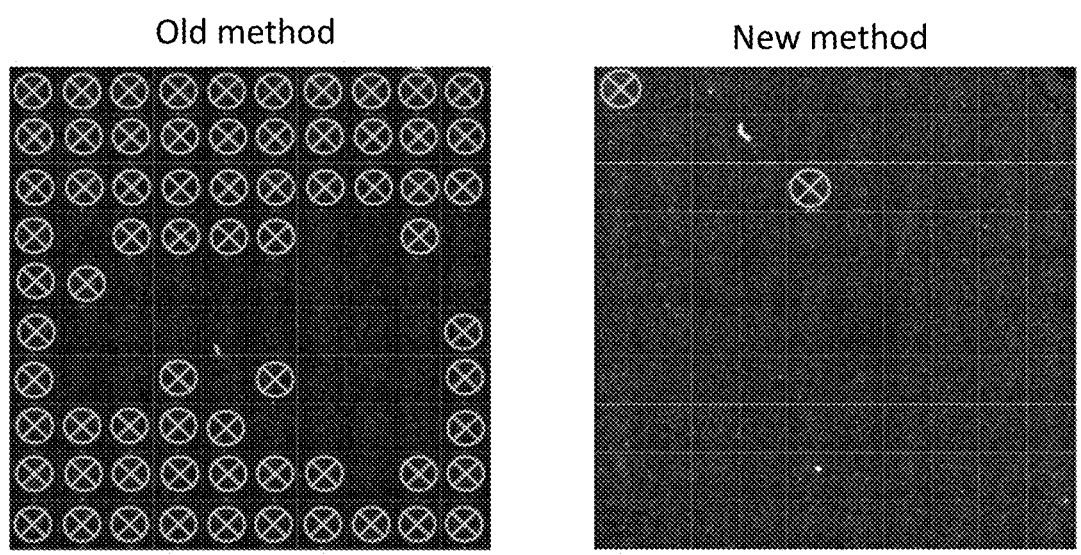
FIG. 3 shows a comparison of data obtained from this method relative to data obtained from an alternative method.

A liquid containing 40,000 to 50,000 fluorescent particles was added to each well after the adhesive had set and the liquid was pulled through the aluminum oxide filter using a vacuum. The fluorescent particles retained on the aluminum oxide filter in each well were imaged using a fluorescence microscope. The depth of field of the microscope (i.e., the area in front of the lens in acceptable focus) was 3.5 microns. Particles become out of focus in a well when the filter portion within the well is insufficiently planer. All the data from a well was eliminated if there were an unacceptable number of particles that are out of focus in the well. In typical experiments, the data from almost 60% (typically 50% to 60%) of the wells is discarded if an assembly made using the old method is used whereas the data from consistently less than 2% of the wells is discarded if an assembly made using the new method is used. FIG. 3 shows typical results obtained using the old method and typical results obtained using the new method, in which the discarded wells are indicated. As such, use of the new method provides more useable data than the old method.

That which is claimed is:

1. A filtration device comprising:
   (a) an open-bottomed multi-well plate;
   (b) a planar spacer that comprises apertures, wherein the positioning and size of the apertures match the positioning and size of the wells of the multi-well plate; and
   (c) a porous capillary membrane;
   wherein:
      (i) the planar spacer is sandwiched between the multi-well plate and the porous capillary membrane,
      (ii) the apertures of the planar spacer are aligned with the wells of the multi-well plate,
      (iii) the planar spacer is bonded to the multi-well plate via an adhesive; and
      (iv) the planar spacer is bonded to the porous capillary membrane via an adhesive.

2. The device of claim 1, wherein the multi-well plate has at least 10 wells.

3. The device of claim 1, wherein the multi-well plate is molded.

4. The device of claim 1, wherein the wells of the multi-well plate of (a) are square or round.

5. The device of claim 1, wherein the adhesive of (iii) is continuous around the bottom of each well of the plate and provides a liquid-tight seal that prevents well to well leakage between adjacent wells of the plate.

6. The device of claim 5, wherein the adhesive of (iv) is continuous around the bottom of each aperture of the planar spacer and provides a liquid-tight seal that prevents leakage between adjacent apertures of the planar spacer.

7. The device of claim 1, wherein the planar spacer is made of a metal or extruded plastic.

8. A kit comprising:
   (a) an open bottomed multi-well plate;
   (b) a porous capillary membrane; and
   (c) a planar spacer that comprises apertures, wherein the positioning and size of the apertures matches the positioning and size of the wells of the multi-well plate.

9. The kit of claim 8, wherein the planar spacer comprises a pre-applied layer of adhesive on one or both sides.

10. The kit of claim 9, wherein the pre-applied layer of adhesive is continuous around each aperture of the planar spacer, on one or both sides.

11. The kit of claim 9, wherein the adhesive is a peel-and-stick adhesive.

12. The kit of claim 9, wherein the planar spacer or tape comprises a pre-applied layer of adhesive that has an average thickness of at least 100 microns on one side and a layer of adhesive that has an average thickness in the range of 30-80 microns on the other side.

13. The kit of claim 8, further comprising a double-sided peel-and-stick adhesive tape, cut to match the grid.

14. A method for making a multi-well filtration device comprising:
   (a) obtaining:
      (i) an open bottomed multi-well plate;
      (ii) a porous capillary membrane; and
      (iii) a planar spacer that comprises apertures, wherein the planar spacer is shaped to match the multi-well plate and the positioning and size of the apertures matches the positioning and size of the wells of the multi-well plate;
   (b) affixing a first side of the planar spacer to the bottom of the open bottomed multi-well plate using an adhesive; and
   (c) affixing the porous capillary spacer to the second side of the planar spacer using an adhesive.

15. The method of claim 14, further comprising allowing the adhesive to set.

16. The method of claim 14, wherein the method comprises:
   (a) producing a layered assembly comprising, in order:
      (i) the open bottomed multi-well plate;
      (ii) the adhesive;
      (iii) the planar spacer;
      (iv) the adhesive; and
      (v) the porous capillary membrane;
   (b) applying a force to press the multi-well plate and porous capillary membrane together so that the multi-well plate, planar spacer, and porous capillary membrane bond together via the adhesive; and (c) removing the force of (b), to produce the multi-well filtration device.

17. The method of claim 16, wherein the adhesive of (ii) is continuous around the bottom of each well of the plate.

18. The method of claim 16, wherein the adhesive of (ii) has an average thickness of at least 100 microns.

19. The method of claim 16, wherein the adhesive of (iv) is continuous around the apertures of the spacer.

20. The method of claim 16, wherein the adhesive of (iv) has an average thickness in the range of 30-80 microns.

\* \* \* \* \*